United States Patent [19]

Ott

[11] Patent Number: 5,674,237
[45] Date of Patent: Oct. 7, 1997

[54] SAFETY TROCAR

[76] Inventor: Henryk Ott, 41917 Osgood Rd., Fremont, Calif. 94539

[21] Appl. No.: 612,451

[22] Filed: Mar. 6, 1996

[51] Int. Cl.[6] .................................................. A61B 17/34
[52] U.S. Cl. ........................ 606/185; 604/264; 606/167
[58] Field of Search ............................... 604/164, 264; 606/167, 170, 171, 184, 185

[56] References Cited

U.S. PATENT DOCUMENTS

| | | | |
|---|---|---|---|
| 4,535,773 | 8/1985 | Yoon | 604/51 |
| 4,601,710 | 7/1986 | Moll | 604/165 |
| 4,654,030 | 3/1987 | Moll et al. | 604/165 |
| 4,931,042 | 6/1990 | Holmes et al. | 604/164 |
| 5,030,206 | 7/1991 | Lander | 604/164 |
| 5,066,288 | 11/1991 | Deniega et al. | 604/274 |
| 5,104,382 | 4/1992 | Brinkerhoff et al. | 604/165 |
| 5,114,407 | 5/1992 | Burbank | 604/164 |
| 5,116,353 | 5/1992 | Green | 604/184 |
| 5,152,754 | 10/1992 | Plyley et al. | 604/164 |
| 5,215,526 | 6/1993 | Deniega et al. | 604/164 |
| 5,224,952 | 7/1993 | Deniega et al. | 604/184 |
| 5,242,427 | 9/1993 | Bilweis | 604/264 |
| 5,248,298 | 9/1993 | Bedi et al. | 604/51 |
| 5,261,891 | 11/1993 | Brinkerhoff et al. | 604/165 |
| 5,267,965 | 12/1993 | Deniega | 604/164 |
| 5,295,993 | 3/1994 | Green | 604/184 |
| 5,314,417 | 5/1994 | Stephens et al. | 604/264 |
| 5,318,585 | 6/1994 | Guy et al. | 604/185 |
| 5,399,167 | 3/1995 | Deniega | 604/264 |
| 5,522,833 | 6/1996 | Stephens et al. | 606/185 |
| 5,562,696 | 10/1996 | Noldes et al. | 606/185 |
| 5,569,291 | 10/1996 | Privitera et al. | 606/185 |
| 5,569,292 | 10/1996 | Scweinberger et al. | 606/185 |
| 5,591,192 | 1/1997 | Privitera et al. | 606/185 |

FOREIGN PATENT DOCUMENTS 2697150   4/1994   France .................................. 606/185

Primary Examiner—Glenn Dawson
Attorney, Agent, or Firm—James J. Leary; Leary, Titus & Aiello

[57] ABSTRACT

A safety trocar device is described which has an internal safety shield within the obturator of the trocar. The internal safety shield is spring loaded to extend in the distal direction to cover the cutting tip of the trocar obturator. In one embodiment, the trocar obturator is made with a three-sided pyramidal cutting tip and the safety shield has three distally extending fingers which extend through openings in the faces of the pyramidal cutting tip. The safety shield with its three distally extending fingers is preferably rounded to an ellipsoidal shape on the distal end to facilitate penetration of the tissues and to reduce frictional resistance to deployment of the safety shield. The obturator and the safety shield are part of a trocar assembly which also includes a shaft and a proximal handle. Optionally, the trocar assembly may also include a safety locking mechanism which prevents premature or unintended withdrawal of the safety shield. The safety mechanism trocar can be used as a stand-alone trocar device or used in conjunction with an access cannula. The safety trocar is safer and more effective in use because the internal safety shield actuates to shield the sharp point of the obturator immediately upon penetrating the body tissue and entering a body cavity.

19 Claims, 9 Drawing Sheets

SAFETY TROCAR

FIELD OF INVENTION

The present invention relates generally to surgical trocars used to puncture tissues to gain access to internal body cavities or to place an access cannula for endoscopic surgery. More particularly, it relates to a surgical trocar which has an internal safety shield which extends to cover the obturator point of the trocar cutting tip immediately after penetrating the body tissue.

BACKGROUND OF THE INVENTION

The term "trocar" originally referred to a pointed device for penetrating body tissues having a pyramidal point with three faces (from the French trois quarts, meaning three-quarters.) By common usage, the term has been broadened to also include devices for placing an access cannula into a body cavity for endoscopic surgery, including laparoscopy, arthroscopy and thoracoscopy. This type of trocar device generally has a cannula, sometimes referred to as a trocar tube, with an obturator within the lumen of the cannula for penetrating the body tissue. The obturator may have a sharpened pyramidal or conical point for puncturing the tissue directly. To place the access cannula, the point of the obturator is pushed through the skin and underlying tissues until the distal end of the cannula is within the body cavity. Then, the obturator is withdrawn, leaving the cannula in place. Alternatively, some trocar devices have a blunt obturator for placing the cannula through a previously made incision.

In the direct puncture technique, sometimes a great deal of force is needed for the obturator point to penetrate the skin and the underlying tissues. When the point of the trocar device breaks through the tissue into the body cavity, there is a sudden drop in resistance and it is possible for the trocar to overshoot its mark and unintentionally puncture or lacerate the internal organs within the body cavity. To prevent this danger of puncturing or damaging the internal organs, various safety mechanisms have been developed for trocar devices. Generally, these safety mechanisms include a spring-loaded tubular safety shield which surrounds the obturator point. The spring of the safety shield compresses allowing the obturator point to be exposed as it penetrates the skin. Once the obturator point has penetrated the tissue, the tubular safety shield springs forward to cover the obturator point.

One such trocar safety mechanism is described in U.S. Pat. No. 4,601,710 granted to Frederic H. Moll for a Trocar Assembly. In one disclosed embodiment, a spring-loaded tubular safety shield resides between the pointed obturator and the access cannula. The tubular safety shield withdraws into the access cannula to expose the pointed obturator as the trocar device penetrates the tissue. A safety locking mechanism prevents premature withdrawal of the safety shield into the access cannula. The safety locking mechanism of this trocar assembly is only effective when the trocar and the access cannula are assembled together. When the trocar is removed from the access cannula it deactivates the safety locking mechanism, reducing the usefulness of this invention as a stand-alone trocar. In another embodiment, a trocar assembly is made up of three blades mounted on the distal end of a shaft. A stationary tubular body surrounds the shaft and the blades. A slotted protective shield, which slides between the shaft and the tubular body, is spring-loaded to move distally to cover the blades of the trocar assembly. The trocar assembly fits into a trocar tube or access cannula.

Another trocar safety mechanism is described in U.S. Pat. No. 5,066,288 granted to Jose C. Deniega and Stephen L. Failla for a Safety Trocar. In one embodiment, the spring-loaded tubular safety shield has a bullet-nosed distal end with a triangular slot through which the obturator passes. When the safety shield is in the fully extended position, the bullet-nosed distal end conforms closely to the pointed tip of the obturator. In another embodiment, the access cannula itself is spring loaded to act as a safety shield.

The external tubular safety shields that are typical of current trocar devices have a number of disadvantages which the present invention seeks to overcome. Because the safety shield is external to the obturator, it is subject to considerable friction against the skin and the tissue that the obturator passes through. This friction can delay the actuation of the safety mechanism by preventing the safety shield from springing forward to cover the tip of the obturator. Sometimes the safety shield will not actuate until the entire obturator tip and the distal end of the access cannula have entered the body cavity. This leaves the sharp point of the obturator exposed for longer than necessary which increases the chances of injury to the internal organs. If a stronger spring is used to overcome the friction, the skin and tissues around the puncture site can become invaginated inward as the safety shield springs forward. If a trocar with an external tubular safety shield is used as a stand-alone trocar without an access cannula surrounding it, there is nothing to relieve the friction on the safety shield, so the safety shield may never actuate.

In one particular laparoscopic trocar technique, known as a Z-puncture, the friction problem is particularly pronounced. To perform the Z-puncture, a 5 mm or 7 mm trocar is inserted through the skin in the lower part of the umbilical pit, pushed 1 cm horizontally in the direction of the symphysis, then turned left or right and pushed 3–4 cm within the subcutaneous fat. Finally, the trocar is set vertically and the trocar is pushed in the direction of the womb through the abdominal musculature and peritoneum. The Z-shaped path of the trocar through the tissue causes enough friction against the safety shield that it is sometimes prevented from actuating at all. It is desirable therefore to provide a trocar safety mechanism which is unaffected by the friction against the tissue through which the trocar passes.

External tubular safety shields also have the disadvantage that, as they spring forward, they can cause a "cookie cutter" action, catching the subcutaneous fat or other tissue between the obturator and the safety shield. This may cause damage to the tissues surrounding the puncture site and may prevent the safety shield from fully actuating which may leave the sharp tip of the obturator exposed. Therefore it is also desirable to provide a trocar safety mechanism which does not cause this "cookie cutter" effect.

In current endoscopic surgical techniques, a trocar may be used in combination with a surgical access cannula or as a stand-alone device to puncture through the skin and underlying tissue for inserting a separate access cannula or a catheter, surgical instrument or endoscope which is to be used without an access cannula. There are different types of access cannulae for different surgical applications. In laparoscopy, where pneumoperitoneum is maintained to create a working space within the abdomen, an access cannula with a gas seal for inserting instruments through is generally used. In arthroscopy, the synovial membranes are typically inflated with saline solution to create a working space within the joints, so arthroscopic access cannulae are generally equipped with fluid seals for inserting instruments through. In thoracoscopic surgery, there is no need to inflate the chest with a fluid because the ribs maintain the shape of the chest cavity. Therefore, a plain cannula without a fluid seal may be used. To create a working space within the chest cavity, one or both lungs can be deflated using a ventilator. In any of these applications, a self anchoring cannula, such as an externally threaded cannula, may be used. It is desirable therefore to provide a safety trocar which is equally effective when used with any kind of cannula or as a stand-alone trocar device.

SUMMARY OF THE INVENTION

In keeping with the foregoing discussion, a primary objective of the present invention is to provide a surgical trocar which is safer and more effective in use than current surgical trocars. One aspect of this objective is to provide a safety mechanism for a surgical trocar which actuates to shield the sharp point of the obturator immediately upon penetrating the body tissue and entering a body cavity. The trocar safety mechanism therefore should be unaffected by the friction of the safety shield against the tissue through which the trocar passes. The trocar safety mechanism should also be free from the undesirable "cookie cutter" effect or any tendency to invaginate the tissue around the puncture site exhibited by previous trocar safety shields. The safety mechanism of the trocar should be equally effective when it is used as a stand-alone trocar or when used in conjunction with an access cannula.

Another objective of the present invention is to provide a safety locking mechanism for the surgical trocar which prevents premature or unintended withdrawal of the safety shield to expose the sharp point of the obturator. One aspect of this objective is to provide a lock-out mechanism that prevents withdrawal of the trocar safety shield until the user has activated a release button near the proximal end of the trocar. Another aspect of this objective is to provide a safety locking mechanism that allows the safety shield to withdraw only once as the trocar tip passes through the tissue and which resets to lock the safety shield in the extended position when it enters the body cavity to protect the internal organs from the sharp point of the trocar. This aspect of the safety lock mechanism will prevent the safety shield from withdrawing again until the release button is actuated a second time. The safety locking mechanism for the safety shield of the trocar should be equally effective when the device is used as a stand-alone trocar or when it is used in conjunction with an access cannula.

In keeping with these objectives, the present invention takes the form of a safety trocar device which has an internal safety shield within the obturator of the trocar. The safety shield is spring loaded to extend in the distal direction to cover the cutting tip of the trocar obturator. In one preferred embodiment, the trocar obturator is made with a three-sided pyramidal cutting tip and the safety shield has three distally extending fingers which extend through openings in the faces of the pyramidal cutting tip. The safety shield with its three distally extending fingers is preferably rounded to an ellipsoidal shape on the distal end to facilitate penetration of the tissues and to reduce frictional resistance to deployment of the safety shield. The obturator and the safety shield are part of a trocar assembly which also includes a shaft and a proximal handle. Optionally, the trocar assembly may also include a safety locking mechanism which prevents premature or unintended withdrawal of the safety shield.

In the direct puncture technique for placing a surgical access cannula, the trocar assembly is used in conjunction with a cannula assembly. A cannula assembly for use in laparoscopic surgery is described having a handle incorporating a hatch port with dual gas seals for insertion of instruments while maintaining pneumoperitoneum. The obturator of the trocar assembly is inserted through the hatch port and through the lumen of the cannula so that the trocar cutting tip and the safety shield extend from the distal end of the cannula. In operation, this trocar/cannula assembly is placed against the skin of the patient at the desired insertion point. (At this point in the procedure, the optional safety lockout mechanism, if one has been included in the trocar assembly, must be actuated to release the safety shield from its locked distal position.) Pressure is placed on the proximal handle to drive the cutting tip through the skin and the underlying tissues. As the obturator penetrates the skin, the safety shield withdraws into the obturator by compressing the spring to expose the cutting tip. As soon as the distal end of the trocar obturator enters a body cavity, the spring urges the safety shield forward to cover the cutting tip to prevent puncturing or lacerating internal organs within the body cavity. (The optional safety lockout mechanism would lock the safety shield in the extended distal position at this point.) Actuation of the safety shield is almost immediate and it is not hindered by friction with the body tissues. The trocar/cannula assembly can be safely advanced until the distal end of the cannula is within the body cavity, then the trocar assembly is withdrawn, leaving the cannula assembly in place. Other objects and advantages of the invention will no doubt occur to those skilled in the art upon reading and understanding the following detailed description along with the accompanying drawings.

BRIEF DESCRIPTION OF THE DRAWINGS

FIG. 8 shows the safety trocar before penetration with the safety shield extended. FIG. 9 shows the safety trocar during penetration with the safety shield retracted. FIG. 10 shows the safety trocar after penetration with the safety shield deployed in the extended position.

DETAILED DESCRIPTION OF THE INVENTION

Figure 1:
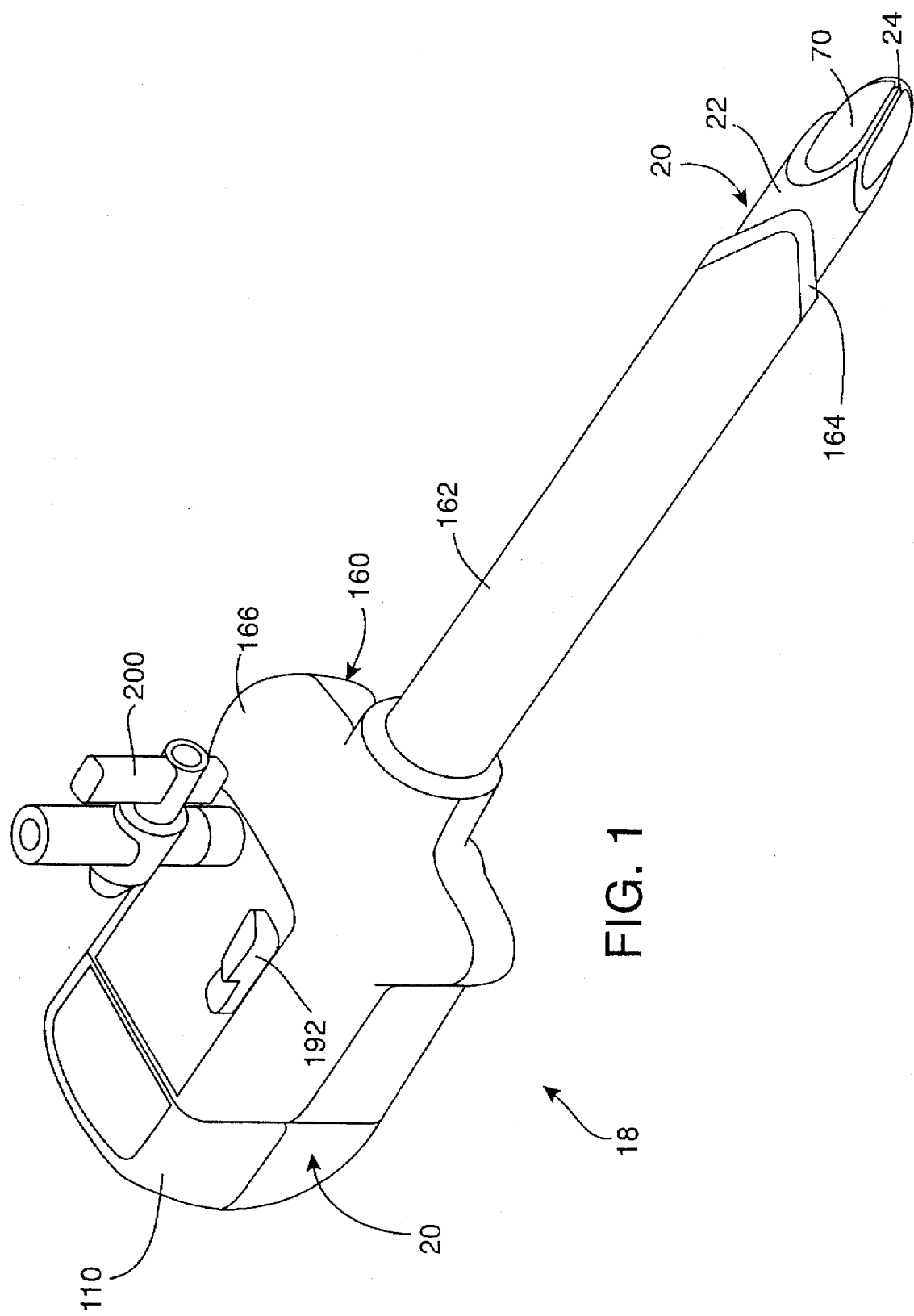
FIG. 1 is a perspective view of the trocar/cannula assembly with the safety shield extended.

FIG. 1 is a perspective view of the safety trocar device of the present invention configured as a trocar/cannula assembly 18 for the direct puncture technique of placing a surgical access cannula. The trocar/cannula assembly 18 includes a trocar assembly 20 and a cannula assembly 160. The trocar assembly 20 is shown inserted through the cannula 162 of cannula assembly 160. The cutting tip 24 of the obturator 22 and the safety shield 70 of the trocar assembly 20 can be seen extending from the distal end 164 of the cannula 162. The safety shield 70 is shown in the extended distal position where the fingers 72, 74, 76 of the safety shield 70 cover the cutting tip 24 of the obturator 22. The trocar/cannula assembly 18 can be made in a wide variety of sizes for different surgical applications. The size of the trocar/cannula assembly 18 is usually given as the nominal inner diameter of the internal lumen 158 of the cannula 162. Typical sizes for the trocar/cannula assembly 18 include 5 mm, 7 mm, 10 mm and 12 mm inner diameter, although many other sizes are possible.

Figure 2:
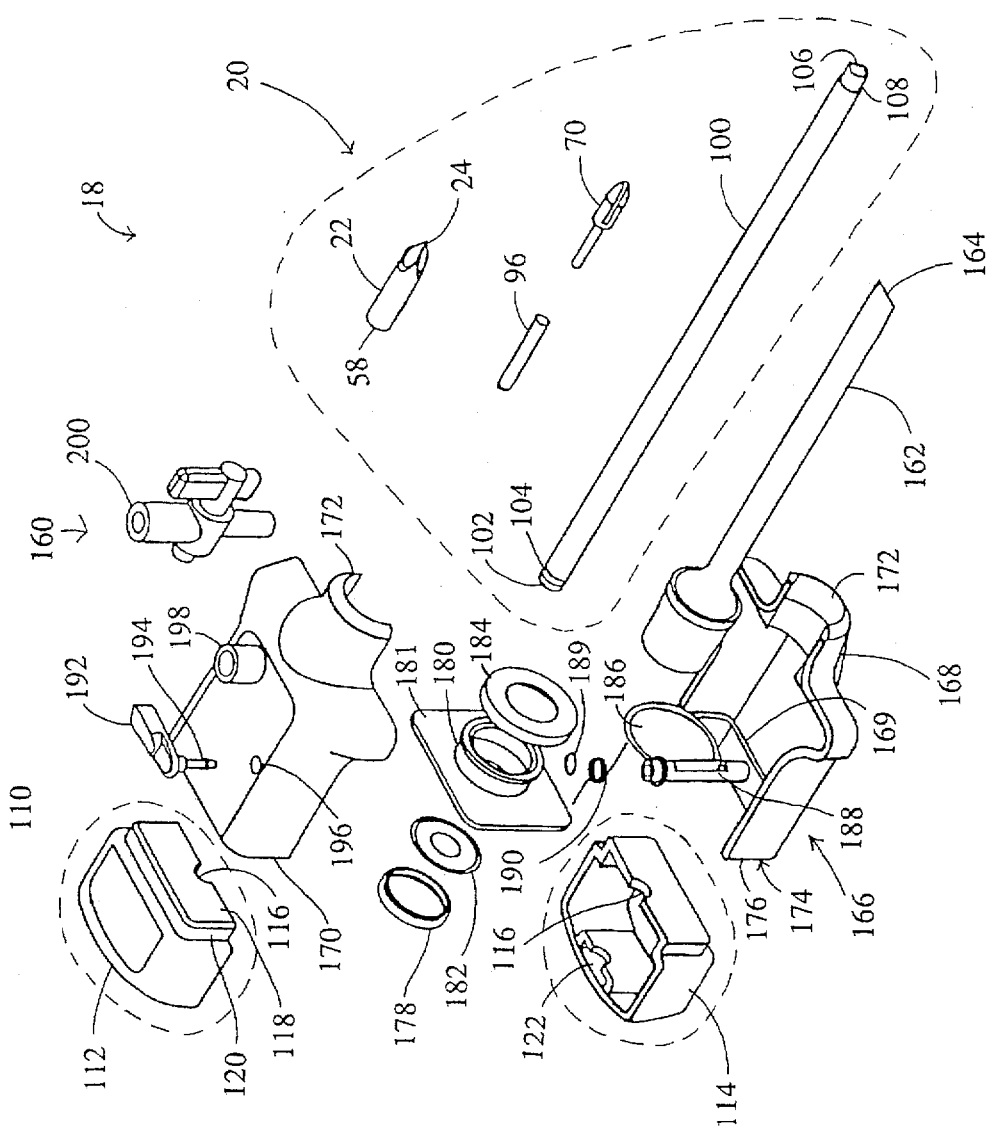
FIG. 2 is an exploded view of the trocar/cannula assembly.

FIG. 2 is an exploded view of the trocar/cannula assembly 18, showing the individual components of the trocar assembly 20 and the cannula assembly 160. The trocar assembly 20 includes an obturator 22 with a distal cutting tip 24. The obturator 22 is mounted on the distal end 106 of a shaft 100. The distal end 106 of the shaft 100 may have a shoulder 108 for attaching the obturator 22 by welding, brazing, soldering or adhesive or it may be threaded for attaching to the obturator 22. The shaft 100 is attached to a trocar handle 110 by inserting the proximal end 102 of the shaft 100 into an attachment hole 116 in the trocar handle 110. In one preferred embodiment of the trocar assembly 20, the trocar handle 110 is made of a front shell 112 and a back shell 114 which are separately injection molded, preferably of polycarbonate or other plastic material, and assembled together using an adhesive, ultrasonic or thermal welding, or by molding interlocking features into the front shell 112 and the back shell 114. In this embodiment, the shaft 100 is attached to the trocar handle 110 by capturing a groove 104 on the proximal end 102 of the shaft 100 in a clip 122 molded into the front shell 112 and a back shell 114. The distal end of the trocar handle 110 is molded with a distal extension 118 surrounded by a shoulder 120 for interlocking with cannula handle 166 of the cannula assembly 160.

The cannula assembly 160 consists of a trocar tube or cannula 162 mounted to a cannula handle 166. Preferably, the cannula 162 is injection molded of polycarbonate or another plastic material. Alternatively, the cannula 162 can be made of a biocompatible metal, such as stainless steel. The cannula 162 has an internal lumen 158 which is sized to be a sliding fit with the exterior of the obturator 22 of the trocar assembly 20. The distal end 164 of the cannula 162 is beveled for facilitating insertion of the trocar/cannula assembly 18 through the skin and underlying tissues of the patient. In one preferred embodiment of the cannula 162, the beveled distal end 164 of the cannula 162 is also angled with respect to the cannula 162 to further facilitate insertion of the trocar/cannula assembly 18. Preferably, the angled distal end 164 of the cannula 162 is at an angle between 30 and 60 degrees, more preferably about 45 degrees, with respect to the cannula 162. In one preferred embodiment of the cannula assembly 160, the cannula handle 166 is made of a front shell 168 and a back shell 170 which are separately injection molded, preferably of polycarbonate or other plastic material, and assembled together using an adhesive, ultrasonic or thermal welding, or by molding interlocking features into the front shell 168 and the back shell 170. The cannula handle 166 is molded with a proximal recess 174 surrounded by a ridge 176 for interlocking with the distal extension 118 of the trocar assembly 20.

For use in laparoscopic surgery, the handle 166 of the cannula assembly 160 is equipped with a hatch port 180 with dual gas seals for insertion of instruments through the cannula 162 while maintaining pneumoperitoneum. The hatch port 180 is located in the center of a flange plate 181 that is adhesively bonded to a ledge 169 within the front shell 168 and the back shell 170 of the handle 166 to close and seal the proximal end of the handle 166. The hatch port 180 has a rear hatch port diaphragm 182 which is a ring shaped seal made of an elastomeric material, such as silicone rubber. The rear hatch port diaphragm 182 has an internal diameter that is slightly smaller than the nominal shaft size of the instruments that will be used through the cannula assembly 160 to create an interference fit that maintains a pneumatic seal around the instrument during use or around the trocar shaft 100 during insertion. For example, the rear hatch port diaphragm 182 may have an internal diameter that is 0.05 to 0.10 inch smaller than the nominal shaft size of the instruments that will be used through the cannula assembly 160. A molded ring retainer 178 holds the rear hatch port diaphragm 182 in place. The ring retainer 178, the hatch port 180 and the flange plate 181 may be molded of polycarbonate or another plastic material. Preferably, the ring retainer 178 is adhesively bonded to the hatch port 180. Spaced slightly ahead of the rear hatch port diaphragm 182 is a front hatch port diaphragm 184, also made of an elastomeric material, such as silicone rubber. The front hatch port diaphragm 184 also has an internal diameter that is slightly smaller than the nominal shaft size of the instruments to be inserted through the cannula assembly 160 to create a pneumatic seal when an instrument is present in the hatch port 180. When there is no instrument shaft inserted through the cannula assembly, a hatch seal 186 is used to create a pneumatic seal. The hatch seal 186 is molded integrally with a pivot shaft 188 which is pivotally mounted within the cannula handle 166. The hatch seal 186 and pivot shaft 188 may be molded of polycarbonate or another plastic material. The hatch seal 186 is a trap door type seal which rotates approximately 90 degrees from a closed position where it seals against the front hatch port diaphragm 184 to an open position to allow instruments or the trocar assembly 20 to be inserted through the hatch port 180. A hatch spring 190 biases the hatch seal 186 toward the closed position. A hatch lever 192 on the exterior of the cannula handle 166 is connected to the hatch seal 186 by a lever shaft 194 that passes through a hole 196 in front shell 168 of the cannula handle 166. The lever shaft 194 may be made with a barb-shaped end that snap fits into a hole in the pivot shaft 188. An O-ring seal 189 creates a gas seal between the end of the pivot shaft 188 and the front shell 168 of the handle 166. The hatch lever 192 can be used to move the hatch seal 186 from the closed to the open position when inserting instruments through the hatch port 180.

A pneumatic gate 200 is mounted on the exterior of the cannula handle 166 distal to the hatch port 180 so that it is in fluid contact with the inner lumen 158 of the cannula 162. The pneumatic gate 200 is a stopcock-type valve which is mounted in a hole 198 molded into the front shell 168 of the cannula handle 166. The pneumatic gate 200 can be connected to a source of pressurized gas such as carbon dioxide for insufflation through the cannula 162 to create or maintain pneumoperitoneum. The pneumatic gate 200 can also be used for venting gases from the peritoneum if desired.

In arthroscopic surgery, the synovial membranes are typically inflated with saline solution rather than a gas to create a clear working space within the joints. Consequently, the gas seals of the hatch port 180 would preferably be replaced with appropriate fluid seals for inserting instruments through while maintaining fluid pressure within the joint. For use in thoracoscopic surgery, the cannula handle 166 can be made without any gas or fluid seals because the ribs maintain the shape of the chest cavity. The cannula handle 166 can even be eliminated and replaced with a simple flange on the proximal end of the cannula 162.

Figure 3A:
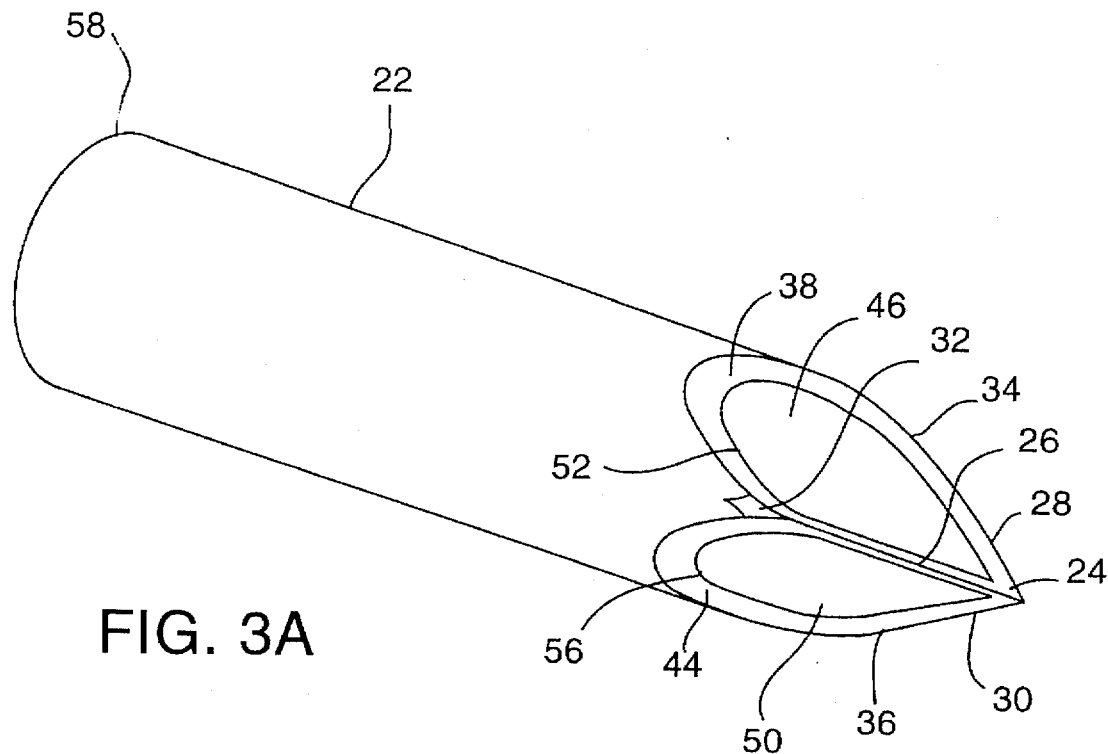
FIG. 3A is a perspective view of the trocar cutting tip.
Figure 3B:
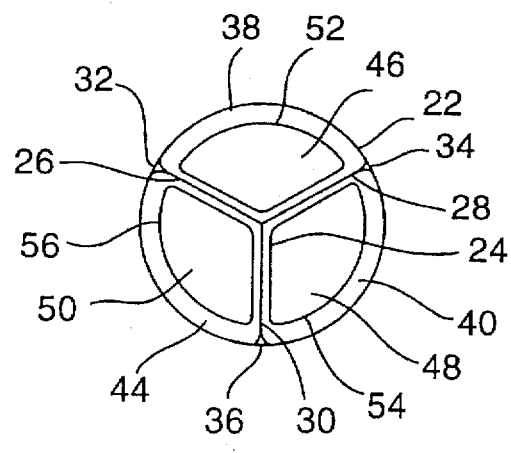
FIG. 3B is a distal end view of the trocar cutting tip.
Figure 4A:
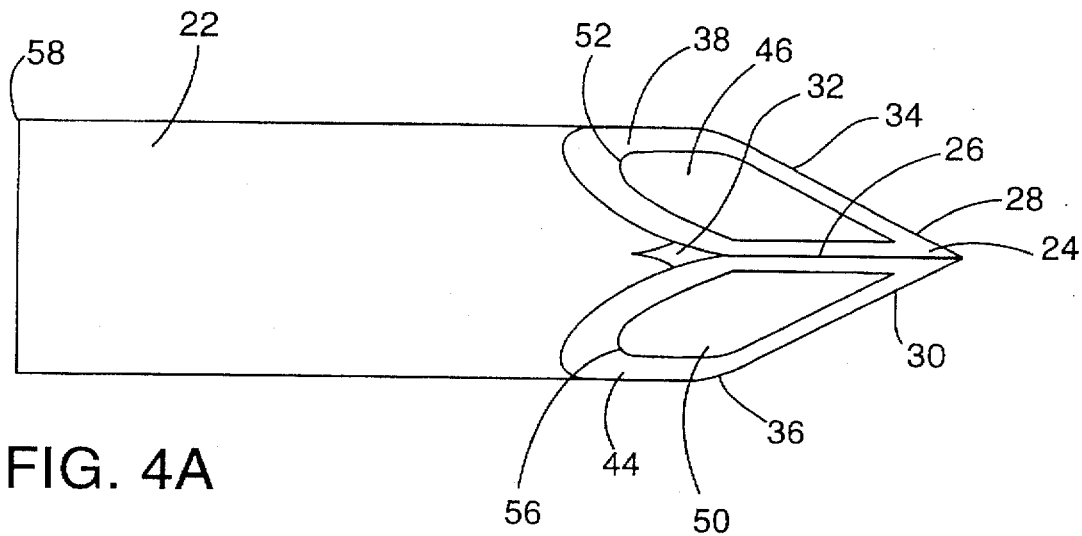
FIG. 4A is a side view of the trocar cutting tip.
Figure 4B:
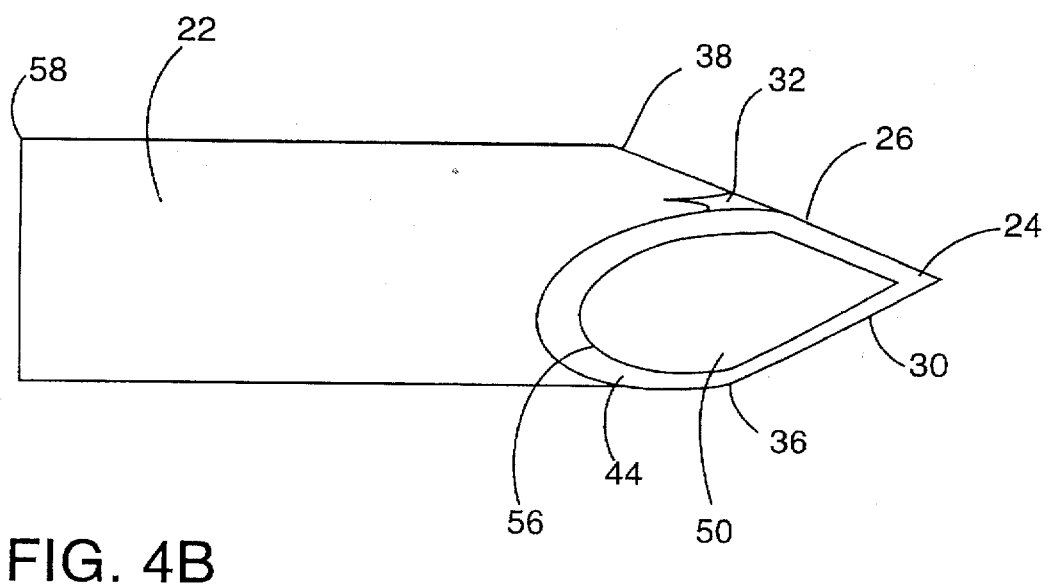
FIG. 4B is a second side view of the trocar cutting tip.

FIGS. 3A, 3B and 4A, 4B illustrate one particularly preferred embodiment of the cutting tip 24 of the trocar obturator 22. FIG. 3A shows a perspective view of the obturator 22 and FIG. 3B shows a distal end view of the cutting tip 24. FIG. 4A and FIG. 4B show two different side views of the obturator 22 and the cutting tip 24. The obturator 22 is preferably made of stainless steel. A hardenable grade of stainless steel, for example precipitation hardenable 17-4PH alloy, is preferred. Alternatively, the obturator 22 may be made of other metals such as titanium or aluminum, or of plastic for disposable trocar devices. The obturator 22 may be made by conventional machining methods, by electrical discharge machining (EDM), or by powder metallurgy or metal injection molding techniques. In this illustrative embodiment, the obturator 22 is made with a three-sided pyramidal cutting tip 24. The three-sided pyramidal cutting tip 24 has three faces 38, 40, 44 that join together at three cutting edges 26, 28, 30. As seen in FIG. 3B, each of the faces 38, 40, 44 has a sector-shaped opening 46, 48, 50 through it for the distally extending fingers 72, 74, 76 of the safety shield 70. The three openings 46, 48, 50 connect to a cylindrical internal cavity 60 within the obturator 22. The proximal edges 52, 54, 56 of the three openings 46, 48, 50 are blunted slightly to avoid coring by the cutting tip 24. The cutting edges 26, 28, 30 of the obturator 22 are ground to a sharp edge along at least the distal part of their length. In one particularly preferred embodiment, the proximal part of each cutting edge 26, 28, 30 is blunted to create three dilating edges 32, 34, 36. In use, the three cutting edges 26, 28, 30 cut a Y-shaped incision in the skin and the underlying tissue of the patient, then the three dilating edges 32, 34, 36 dilate the incision without cutting it further. This creates a smaller incision in the patient which may be quicker to heal, and the dilating action creates a better gas seal around the cannula 162 for maintaining pneumoperitoneum.

Other geometries of the cutting tip 24 of the obturator 22 are possible. For example, the three sharpened cutting edges 26, 28, 30 may extend all of the way to the outer diameter of the obturator 22 with no blunted dilating edges, as shown in the examples in FIGS. 1 and 2. Otherwise, only one or two of the three cutting edges 26, 28, 30 may sharpened and the remaining edges left blunt as dilating edges. These configurations would make a single line incision or a V-shaped incision respectively, with the rest of the incision being dilated for entry of the cannula 162. Another alternate geometry would have the three faces 38, 40, 44 of the cutting tip 24 hollow ground to create even sharper cutting edges 26, 28, 30 between the faces. A four-sided pyramidal cutting tip would also be possible. Also, the obturator could be made with a conical cutting tip that would puncture the skin at only one point and dilate the incision the rest of the way. This geometry may be especially effective for small diameter trocar devices of 5 mm in diameter or less. Since a conical cutting tip does not have distinct faces, it may be made with one, two or three openings through it for a like number of distally extending fingers on the safety shield 70.

The proximal end 58 of the obturator 22 may also take one of several possible geometries. In the illustrative embodiment of 3A, 3B and 4A, 4B, the proximal end 58 of the obturator 22 is a simple extension of the cylindrical body of the obturator 22 which matches up with the outer diameter of the trocar shaft 100 (FIG. 2). The shoulder 108 on the distal end 106 of the trocar shaft 100 fits into the cylindrical internal cavity 60 of the obturator 22 and is joined by welding, brazing, soldering, adhesive or threading. This geometry may be preferable for small diameter trocar devices of 5 mm diameter or less. For larger trocar devices, it may be preferable to have a shaft 100 with a diameter smaller than the outer diameter of the obturator 22, for example having a 5 mm diameter shaft 100 with a 10 mm or 12 mm diameter obturator 22. The smaller diameter shaft 100 saves weight and material and avoids causing a set in the material of the front and rear hatch port diaphragms 184, 182 from prolonged insertion. In this case, the proximal end of the obturator 24 includes a transition piece 62, as shown in the example in FIG. 8. The transition piece 62 makes a smoothly tapered transition from the larger diameter of the obturator 22 to the smaller diameter of the shaft 100. For situations where there is a only a small difference between the diameter of the obturator 22 and the diameter of the shaft 100, for instance a 7 mm obturator 22 mounted on a 5 mm shaft 100, the transition taper can be machined directly onto the proximal end 58 of the obturator 22 without the need for a separate transition piece 62.

Figure 5A:
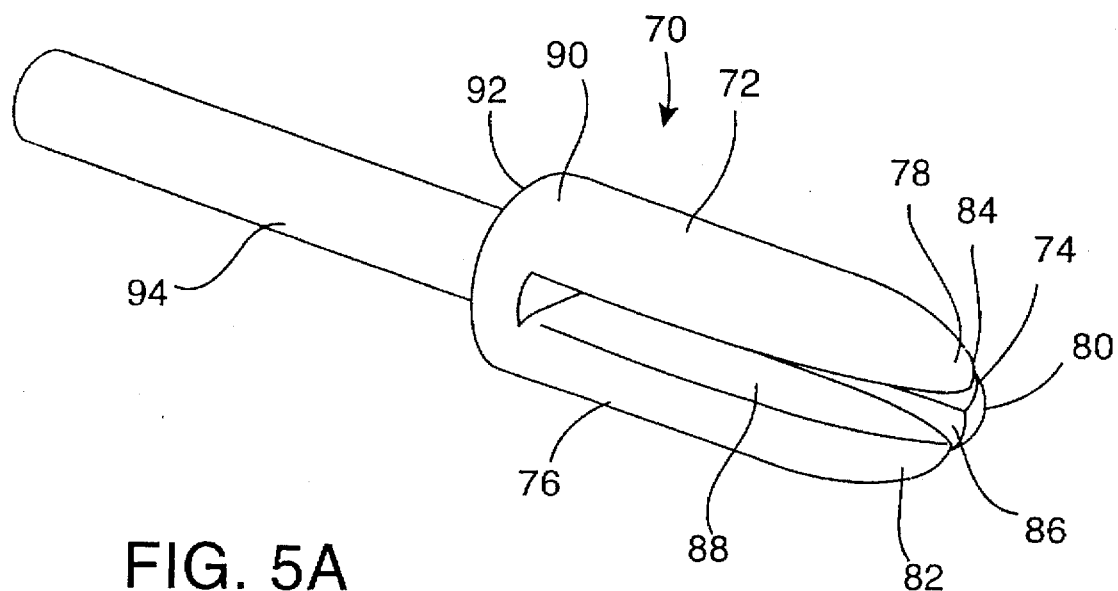
FIG. 5A is a perspective view of the trocar safety shield.
Figure 5B:
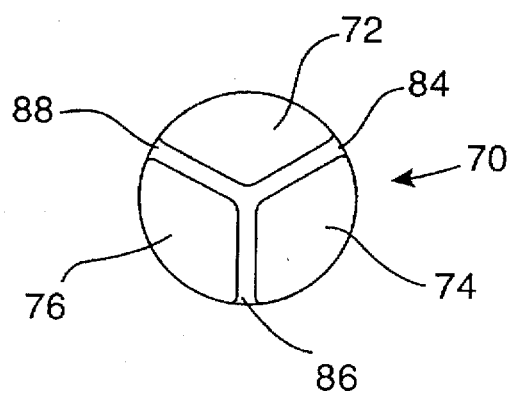
FIG. 5B is a distal end view of the trocar safety shield.
Figure 6A:
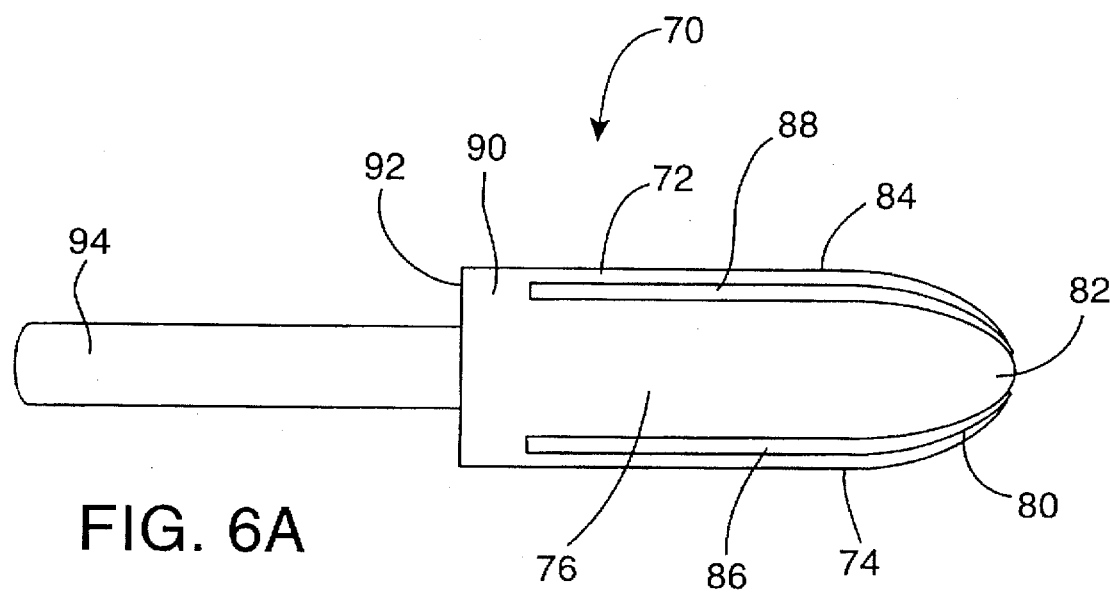
FIG. 6A is a side view of the trocar safety shield.
Figure 6B:
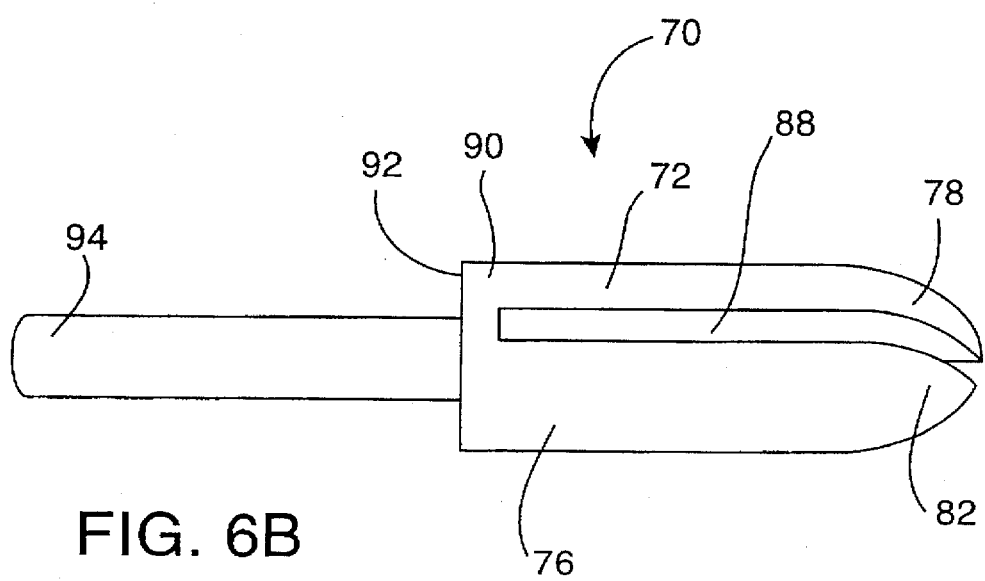
FIG. 6B is a second side view of the trocar safety shield.

FIGS. 5A, 5B and 6A, 6B illustrate one preferred embodiment of the trocar safety shield 70. FIG. 5A shows a perspective view of the safety shield 70 and FIG. 5B shows a distal end view of the safety shield 70. FIG. 6A and FIG. 6B show two different side views of the trocar safety shield 70. The safety shield 70 is preferably made of polycarbonate or another plastic material. The safety shield 70 may be made by conventional machining methods or by injection molding. The safety shield 70, in this illustrative embodiment, has three distally extending fingers 72, 74, 76. The distally extending fingers 72, 74, 76 are generally sector-shaped with rounded corners and are separated by slots 84, 86, 88, as seen in the end view of FIG. 5A. The three distally extending fingers 72, 74, 76 are shaped to have a sliding fit within the sector-shaped openings 46, 48, 50 through the faces 38, 40, 44 of the obturator cutting tip 24. Preferably, the distal ends 78, 80, 82 of the fingers 72, 74, 76 are smoothly rounded. As best seen in FIGS. 6A and 6B, in this exemplary embodiment the distal ends 78, 80, 82 of the fingers 72, 74, 76 are rounded to give the distal end of the safety shield 70 an overall ellipsoidal shape. Other shapes for the distal ends 78, 80, 82 of the fingers 72, 74, 76, such as conical or spheroidal, are possible. The fingers 72, 74, 76 are joined together by the cylindrical proximal portion 90 of the safety shield 70. This proximal portion 90 of the safety shield 70 is sized to have a sliding fit within the cylindrical internal cavity 60 of the obturator 22.

Figure 8:
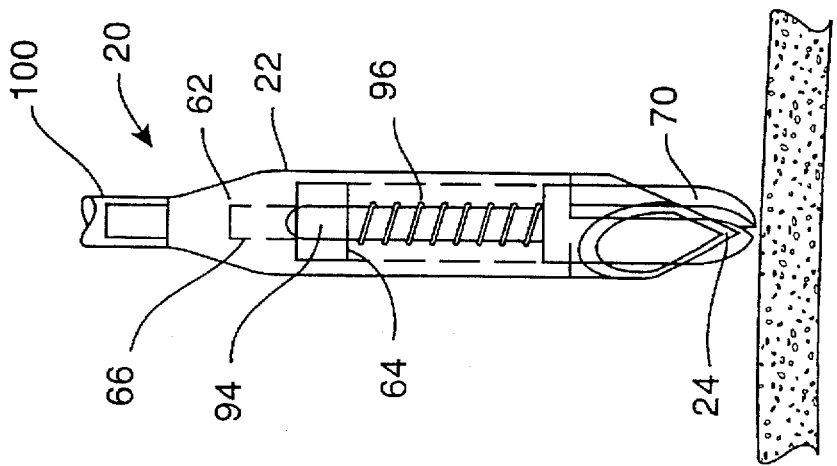

Extending proximally from the shoulder 92 on the proximal portion 90 of the safety shield 70 is a pin 94 that is sized to fit through the center of the helical spring 96 (see FIG. 2 or FIG. 8). The pin 94 is also sized to have a sliding fit within a cylindrical hole 66 formed in either the distal end 106 of the shaft 100 (FIG. 2) or the transition piece 62 (FIG. 8), depending on the configuration of the obturator 22. When the trocar assembly 20 is assembled, the helical spring 96 is captured between the shoulder 92 on the proximal end 90 of the safety shield 70 and either the distal end 106 of the shaft 100 (FIG. 2) or the shoulder 64 on the distal end of the transition piece 62 (FIG. 8). The helical spring 96 urges the safety shield 70 in the distal direction so that the distally extending fingers 72, 74, 76 of the safety shield 70 surround and protect the cutting tip 24 and the cutting edges 26, 28, 30 of the obturator 22.

Figure 7:
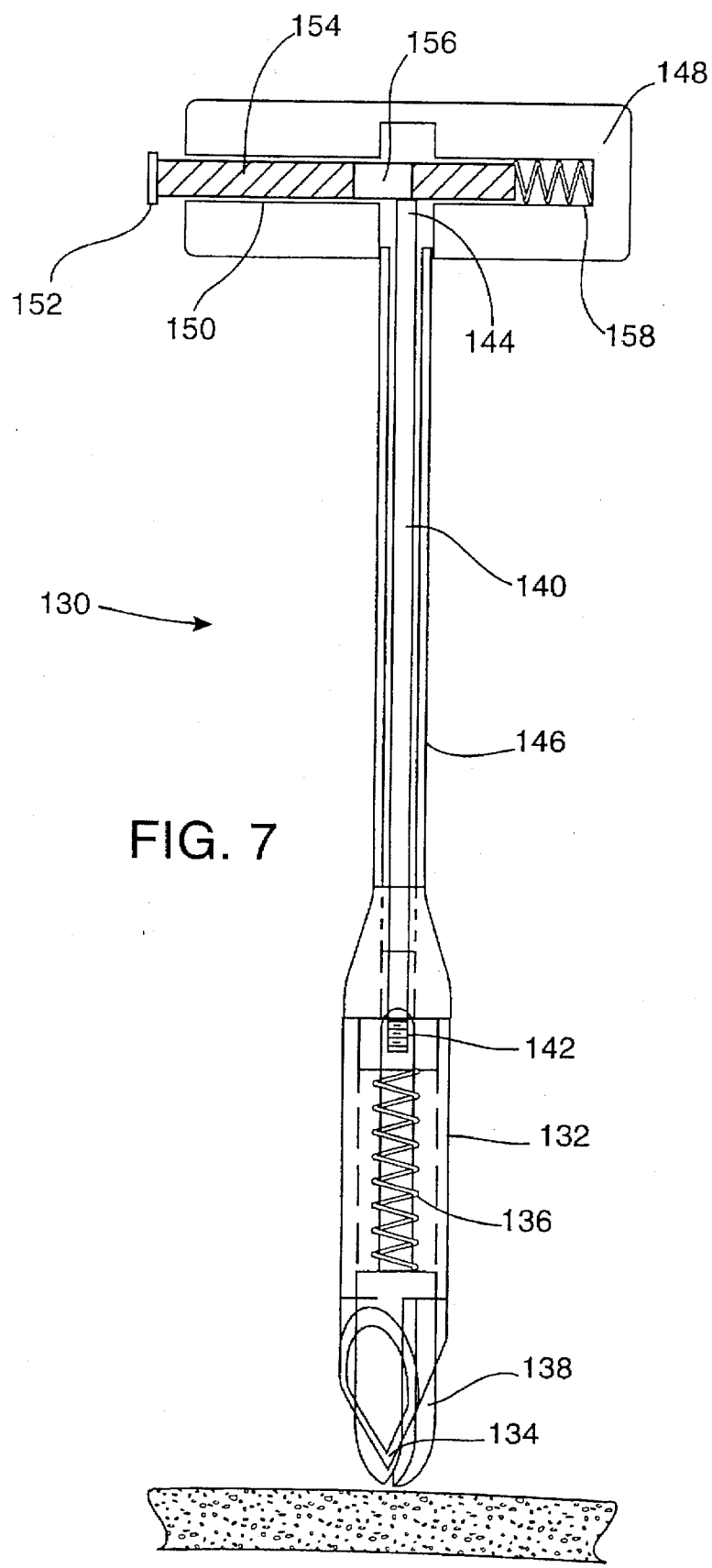
FIG. 7 is a cross section of a safety trocar with a safety lock mechanism incorporated therein.

FIG. 7 shows a cross section of an alternate embodiment of the safety trocar device of the present invention incorporating an optional safety lock mechanism. The trocar assembly 130 is pictured separately to demonstrate that the safety lock mechanism is designed to work equally well when the trocar assembly 130 is used as a stand-alone trocar device or when it is used in conjunction with a cannula assembly 160. In this embodiment, the proximal end of the safety shield 138 is attached to a push rod 140 which extends through a hollow tubular shaft 146 that is attached to the trocar handle 148. The distal end 142 of the push rod 140 may be threaded into the proximal end of the safety shield 138 or it may be attached by an adhesive or other means. There is a transverse bore 150 within the trocar handle 148 into which a compression spring 158 and a plunger 154 with an attached safety release button 152 are inserted. The plunger 154 has a sliding fit within the transverse bore 150. There is a hole or opening 156 through the plunger 154 that is misaligned with the proximal end 144 of the push rod 140 when the plunger 154 is in its rest position with the compression spring 158 extended. When the safety release button 152 is pressed, the plunger 154 moves to the right, compressing the compression spring 158 and aligning the opening 156 through the plunger 154 with the proximal end 144 of the push rod 140. Thus, when the safety release button 152 is pressed, the safety shield 138 is free to move proximally to expose the cutting tip 134 of the obturator 132 during insertion of the trocar device through the skin of the patient. Once the incision is started, the operator can release the safety release button 152. When the cutting tip 134 of the obturator 132 enters the body cavity, the helical spring 136 moves the safety shield 138 distally to cover the cutting tip 134 of the obturator 132. The safety release button 152 will pop out indicating that the safety shield 138 has deployed and the safety lock mechanism will insure that the safety shield 138 will not move proximally to expose the cutting tip 134 a second time unless the safety release button 152 is pressed again. In this way, the safety lock mechanism prevents the trocar device from inadvertently penetrating any of the internal organs within the body cavity.

OPERATIONAL DESCRIPTION

Figure 10:
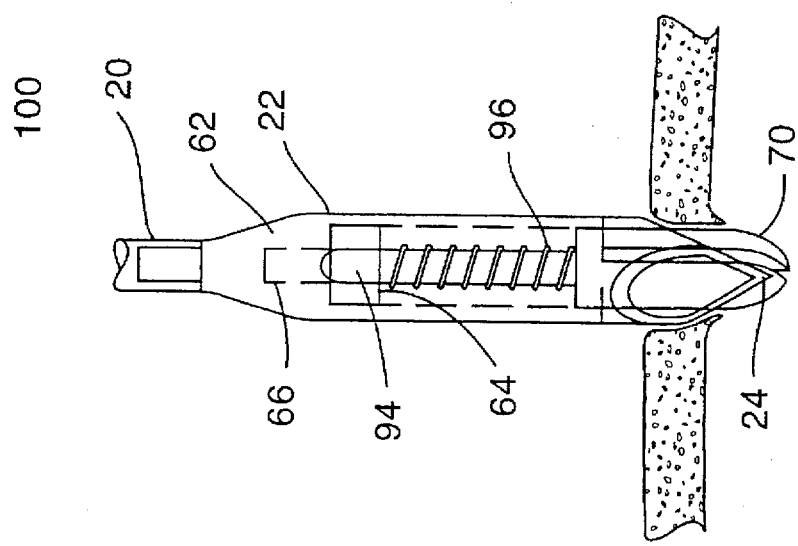
FIGS. 8, 9 and 10 are a series of drawings showing the operation of the safety trocar.
Figure 9:
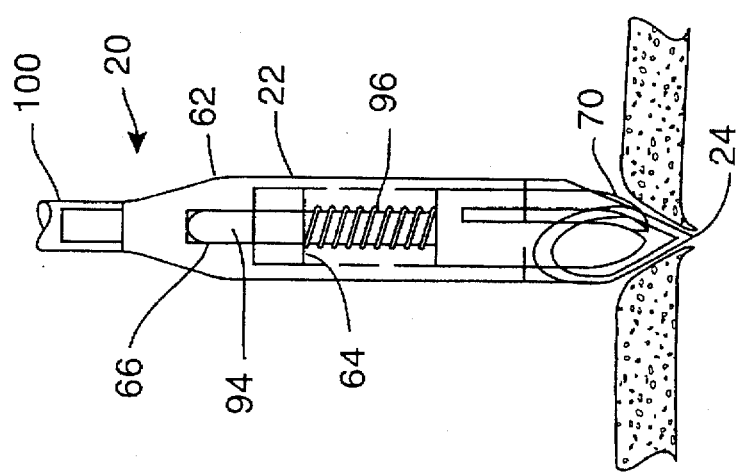

FIGS. 8, 9 and 10 show the operation of the safety trocar of the present invention for creating a surgical incision. Once again, the trocar assembly 20 has been pictured separately, but it is important to note that the trocar assembly 20 can be used separately as a stand-alone trocar device or used in conjunction with a cannula assembly 160, as described above in relation to FIGS. 1 and 2. FIG. 8 shows the trocar assembly 20 approaching the patient's skin before penetration with the safety shield 70 extended in the distal position to cover the cutting tip 24 of the obturator 22. When the safety shield 70 contacts the patient's skin, the helical spring 96 begins to compress, allowing the safety shield 70 to move proximally to expose the cutting tip 24 of the obturator 22. In FIG. 9 the cutting tip 24 of the obturator 22 has penetrated the patient's skin and the underlying tissues, and the safety shield 70 is retracted to its most proximal position. Once the cutting tip 24 of the obturator 22 has broken through the skin and the underlying tissues and entered the body cavity, the helical spring 96 immediately urges the safety shield 70 forward to the extended distal position to cover the cutting tip 24 of the obturator 22, as shown in FIG. 10. With the cutting tip 24 covered, the trocar assembly 20 can be safely advanced further into the body cavity to complete the incision or to install the cannula assembly 160 without worry of puncturing or lacerating the internal organs within the body cavity. After the incision is complete, the trocar assembly 20 is withdrawn, leaving the cannula assembly 160 in place to provide surgical access to the internal body cavity.

Because the safety shield 70 is internal to the trocar obturator 22, there is very little friction against the tissue to interfere with the deployment of the safety shield 70 once the cutting tip 24 has entered the body cavity. Deployment of the internal safety shield 70 is, in fact, measurably faster than that of previous tubular external safety shields. The friction against the surrounding tissues delays the deployment of the external safety shields. In some cases, an external safety shield will not even deploy until the cannula tip is pushed through the incision to relieve the friction between the safety shield and the surrounding tissue. This leaves the cutting tip of the trocar exposed for an unnecessarily long time, increasing the chances of inadvertently damaging an internal organ. The faster deployment of the internal safety shield in the safety trocar of the present invention increases patient safety and enhances the positive outcome of endoscopic surgery using a percutaneous trocar incision or a surgical access cannula.

Figure 12:
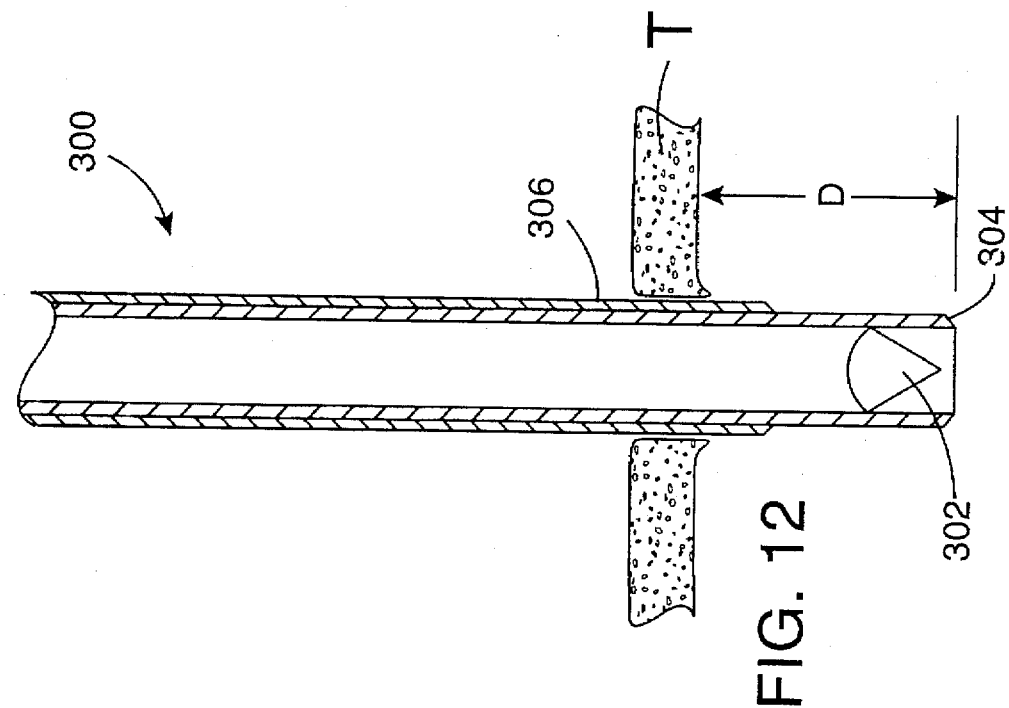
FIGS. 11 and 12 show a side-by-side performance comparison between the safety trocar of the present invention in FIG. 11 and a prior art safety trocar having a tubular safety shield in FIG. 12.
Figure 11:
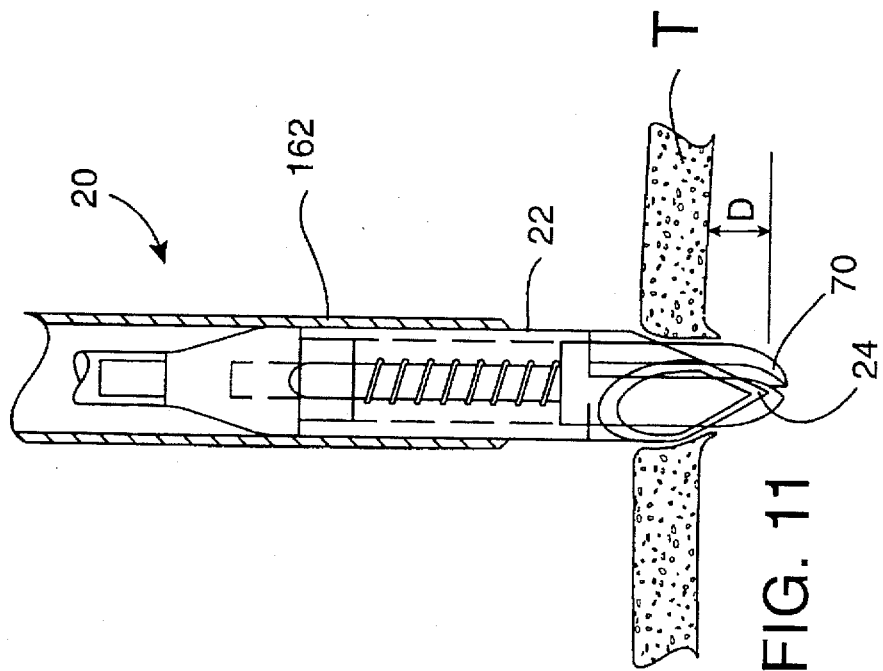

FIGS. 11 and 12 show a side-by-side performance comparison based on laboratory testing between the safety trocar of the present invention 20 and a prior art safety trocar 300 having a tubular safety shield 304. The performance of the two safety trocars was evaluated on the basis of how well the safety shield would protect the internal organs from inadvertent puncture or laceration by the cutting tip of the trocar during placement of an access cannula into the body. This was judged by how far the cutting tip of the trocar must penetrate into the body cavity before the safety shield deploys. In FIG. 11, the safety trocar 20 of the present invention is shown after the trocar cutting tip 24 has penetrated the skin and underlying tissue T of a simulated patient at the exact moment when the internal safety shield 70 deploys to cover the point of the trocar cutting tip 24. The distance that the cutting trocar cutting tip 24 has penetrated into the body cavity when the safety shield 70 deploys is indicated by the letter D. This penetration distance D has been shown to be approximately 6.4 millimeters in repeated laboratory testing with a 12 millimeter trocar 22 and cannula 162. FIG. 12 shows a prior art safety trocar 300 with a tubular safety shield 304 tested under the same laboratory conditions. The safety trocar 300 is shown after the trocar cutting tip 302 has penetrated the skin and underlying tissue T of the simulated patient at the exact moment when the tubular safety shield 304 deploys to cover the point of the trocar cutting tip 302. The distance that the cutting trocar cutting tip 302 has penetrated into the body cavity when the safety shield 70 deploys is indicated by the letter D. This penetration distance D has been shown to be approximately 25.4 millimeters in repeated laboratory testing with a commercially available 12 millimeter trocar 302 and cannula 306. The greater penetration distance D for the prior art safety trocar 300 is caused by the friction between the tubular safety shield 304 and the surrounding tissue T. The tubular safety shield 304 does not actually deploy until the distal tip of the cannula 306 is pushed through the incision to relieve the friction between the tubular safety shield 304 and the surrounding tissue T. Because the prior art safety trocar 300 must penetrate farther into the body cavity before deployment of the safety shield 304 there is a greater risk of inadvertently puncturing or lacerating the internal organs within the body cavity.

Another advantage of the present invention that has been demonstrated by laboratory testing is that it takes less force to penetrate the skin and underlying tissue T of the patient using the present safety trocar 20 with the internal safety shield 70 compared to the commercially available prior art safety trocar 300 with a tubular safety shield 304. This is because of the additional force needed to push the blunt distal edge of the external tubular safety shield 304 of the prior art safety trocar 300 through the skin and underlying tissue T. The reduced penetration force also lends to the improved safety provided by the present invention. Because less force is required to penetrate the skin and underlying tissue, it is less likely that the surgeon will overshoot when making an incision and push the trocar point too far into the body cavity where it may damage the internal organs.

Although the examples given include many specificities, they are intended as illustrative of only some of the possible embodiments of the present invention. Other embodiments and modifications will, no doubt, occur to those skilled in the art. For example, the safety trocar of the present invention could be modified to use an obturator with an electrosurgical or ultrasonic cutting tip for penetrating the patient's skin and underlying tissue in place of the sharpened cutting tip shown. Thus, the examples given should only be interpreted as illustrations of some of the preferred embodiments of the invention, and the full scope of the invention should be determined by the appended claims and their legal equivalents.

I claim:

1. A safety trocar device comprising:

a trocar obturator having a pyramidal distal end with a tissue penetrating tip and a plurality of edges, said trocar obturator having an internal cavity and at least one opening through said distal end connecting with said internal cavity, at least one of said plurality of edges having a sharpened distal part defining a cutting edge and a blunted proximal part defining a dilating edge, a safety shield slidably received within said internal cavity of said trocar obturator, said safety shield having at least one distally extending finger slidably received within said at least one opening through said distal end, said safety shield having a distal position in which said at least one distally extending finger covers said tissue penetrating tip of said trocar obturator and a proximal position in which said tissue penetrating tip of said trocar obturator is exposed, and a means for biasing said safety shield to move from said proximal position to said distal position.

2. The safety trocar device of claim 1 wherein said safety shield has a plurality of distally extending fingers slidably received within a plurality of openings through said distal end of said trocar obturator.

3. The safety trocar device of claim 1 wherein said pyramidal distal end of said trocar obturator is a three-sided pyramidal cutting tip.

4. The safety trocar device of claim 3 wherein said safety shield has three distally extending fingers slidably received within three openings through said distal end of said trocar obturator.

5. The safety trocar device of claim 3 wherein said three-sided pyramidal cutting tip of said trocar obturator has three edges, each edge having a sharpened distal part defining three cutting edges and a blunted proximal part defining three dilating edges.

6. The safety trocar device of claim 5 wherein said safety shield has three distally extending fingers slidably received within three openings through said distal end of said trocar obturator which cover said three cutting edges when said safety shield is in said distal position.

7. The safety trocar device of claim 3 wherein said three-sided pyramidal cutting tip of said trocar obturator has three edges, each edge having a sharpened distal part defining three cutting edges and a blunted proximal part defining three dilating edges and a smooth, uninterrupted transition between said sharpened distal part and said blunted proximal part.

8. The safety trocar device of claim 1 further comprising a safety lock means for selectively preventing said safety shield from moving from said distal position to said proximal position.

9. The safety trocar device of claim 8 wherein said safety lock means has a locked mode in which said safety shield is prevented from moving from said distal position to said proximal position and a release mode in which said safety shield is permitted to move from said distal position to said proximal position.

10. The safety trocar device of claim 9 wherein when said safety lock means is in said release mode, said safety lock means operates to allow said safety shield to move from said distal position to said proximal position only once and when said safety shield returns to said distal position, said safety lock means returns to said locked mode to prevent said safety shield from moving from said distal position to said proximal position.

11. The safety trocar device of claim 1 wherein said trocar obturator is mounted on an elongated shaft.

12. The safety trocar device of claim 11 wherein said trocar obturator has a first diameter and said elongated shaft has a second diameter which is smaller than said first diameter.

13. The safety trocar device of claim 11 further comprising a trocar handle attached to a proximal end of said elongated shaft.

14. The safety trocar device of claim 1 further comprising a tubular cannula having an internal lumen slidably received around said trocar obturator.

15. The safety trocar device of claim 14 further comprising a fluid seal means at a proximal end of said tubular cannula.

16. The safety trocar device of claim 15 wherein said fluid seal means includes a rotatable hatch seal for selectively sealing said proximal end of said tubular cannula.

17. The safety trocar device of claim 15 wherein said fluid seal means includes a ring shaped elastomeric seal for sealing around an instrument placed through said tubular cannula.

18. The safety trocar device of claim 15 further comprising a means for introducing a fluid into said tubular cannula distal to said fluid seal means.

19. The safety trocar device of claim 1 wherein said safety shield comprises a pin extending from a proximal end of said safety shield, and wherein said means for biasing said safety shield to move from said proximal position to said distal position comprises a helical compression spring surrounding said pin.

* * * * *